(12) United States Patent
Paaren et al.

(10) Patent No.: US 6,448,419 B1
(45) Date of Patent: Sep. 10, 2002

(54) SYNTHESIS OF 2-HYDROXYESTRADIOL DERIVATIVES

(75) Inventors: Herbert E. Paaren, Madison; Steven R. Duff, Middleton, both of WI (US)

(73) Assignee: Tetrionics, Inc., Madison, WI (US)

( * ) Notice: Subject to any disclaimer, the term of this patent is extended or adjusted under 35 U.S.C. 154(b) by 0 days.

(21) Appl. No.: 09/923,744

(22) Filed: Aug. 7, 2001

(51) Int. Cl.$^7$ ............................... C07J 5/00; C07J 7/00
(52) U.S. Cl. ................... 552/505; 552/558; 552/505
(58) Field of Search ......................... 552/505, 558

(56) References Cited

U.S. PATENT DOCUMENTS 5,789,607 A * 8/1998 Okabe ..................... 552/505

OTHER PUBLICATIONS

Diorazio et al. (DN 116:214765, CAPLUS, abstract of J. Chem. Soc., Perkisn Trans 1 (1992), (4), 421–5).*
Minailova et al. (DNA 99:71076, CAPLUS, abstract of Zh. Obshch. Khim. (1983), 53(3), 622–634).*
Pokrovskaya et al. (DN 96:63190, CAPLUS, abstract of Probl. Endokrinol. Khim.(1981), 27(6), 66–70).*

* cited by examiner

Primary Examiner—Sabiha Qazi
(74) Attorney, Agent, or Firm—Ryndak & Suri

(57) ABSTRACT

Disclosed is a method of preparing 2-hydroxy-3,17β-estradiol derivatives wherein 3,17β-estradiol is reacted with an organolithium reagent and reacted with either a boron reagent or a silicon reagent to form either a 2-boronyl or a 2-silyl modified estradiol analog represented by the corresponding structural formulae:

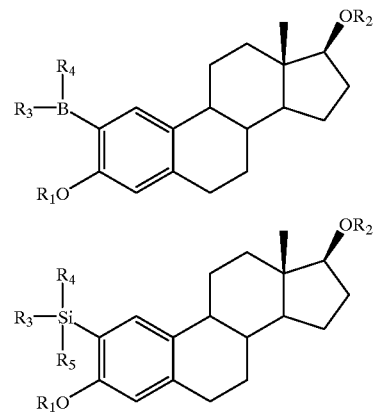

$R_1$ and $R_2$ are each independently a hydroxyl protecting group. $R_3$, $R_4$ and $R_5$ are selected from the group consisting of halogens, alkyl, aryl, hydroxy, substituted or unsubstituted alkyl, and substituted or unsubstituted aryl.

9 Claims, No Drawings

SYNTHESIS OF 2-HYDROXYESTRADIOL DERIVATIVES

FIELD OF THE INVENTION

The present invention is directed to an improved method for synthesizing 2-hydroxy-3,17β-estradiol derivatives and new intermediate compounds useful in synthesizing such estradiol derivatives.

BACKGROUND OF THE INVENTION

Originally discovered as an in vivo metabolite of 3,17β-estradiol, 2-methoxyestradiol has recently been shown to strongly inhibit vascularization of solid tumors making it a potential anticancer agent. Other 2-alkoxy-estradiol derivatives also possess potent anti-angiogenesis properties. A critical intermediate in the synthetic production of these 2-alkoxy-estradiol derivatives is 3,17β-protected 2-hydroxy-estradiol. The family of biologically active 2-alkoxy analogs are most commonly produced from alkylation of the corresponding 3,17β-protected 2-hydroxy analog.

A number of synthetic procedures exist for the production of 2-hydroxyestradiol and its subsequent conversion to the 2-alkoxy analogs. The most popular approach has been to prepare the 2-formyl-estradiol analog, treat it with an organic peracid under Baeyer-Villiger conditions and hydrolyze the resulting formate ester to the 2-hydroxy derivative. Although affording reasonable yields, these multi-step schemes are technically involved and require chromatographic purification at one or more steps. Other more direct approaches such as direct oxygenation of 2-lithiated estradiol analogs suffer from low yields and laborious purifications. Direct introduction of the 2-methoxy moiety via organometallic activation of the estradiol aromatic A-ring has been achieved. However, the difficult preparation and cost of the organometallic reagent make this synthesis unsuitable for large-scale use.

Given the anti-cancer potential of 2-alkoxy-estradiol derivatives, a need exists for a practical, scalable, high yielding and direct synthetic procedure for manufacture of such compounds.

SUMMARY OF THE INVENTION

The present invention is directed to an improved method for synthesizing 2-hydroxy-3,17β-estradiol derivatives and to intermediate compounds that are useful to produce such estradiol compounds. In particular, the present invention is directed to the preparation of 2-boronyl or 2-silyl modified estradiol analogs.

In accordance with the present invention, 3,17β-estradiol is reacted with a suitable organolithium reagent and either a suitable boron reagent or a suitable silicon reagent to form a compound represented by one of the corresponding structural formulae, respectively:

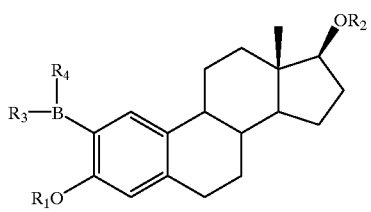

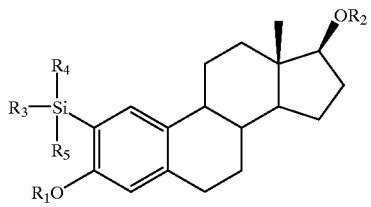

(If a boron reagent) (If a silicon reagent)
where $R_1$ and $R_2$ can be the same or different and each represents an alkaline stable hydroxy protecting group. Preferably, $R_1$ and $R_2$ are each methoxymethyl. $R_3$, $R_4$ and $R_5$ are selected from the group consisting of halogens, alkyl, aryl, hydroxy, substituted or unsubstituted alkoxy, and substituted or unsubstituted aryl.

The organolithium reagent is preferably sec-butyllithium. The silicon and boron reagents are represented by the following corresponding formulae:

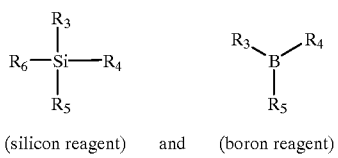

(silicon reagent) and (boron reagent)

(silicon reagent) and (boron reagent)
$R_3$, $R_4$, $R_5$, and $R_6$ are selected from the group consisting of halogens, alkyl, aryl, hydroxy, substituted or unsubstituted alkoxy, and substituted or unsubstituted aryl. Preferably, the silicon reagent is either dichlorodimethylsilane or diethoxydimethylsilane. Trimethyl borate is the preferred boron reagent.

The boronyl or silyl modified estradiol is subsequently oxidized to form the compound represented by the following structural formula:

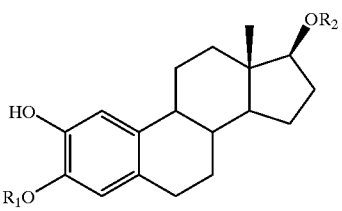

where $R_1$ and $R_2$ are as described above. Sodium perborate is the preferred oxidizing agent for the boronyl derivative. Hydrogen peroxide is the preferred oxidizing agent for the silyl derivative.

The present invention is further directed to novel 2-boronyl or 2-silyl modified estradiols and methods of preparing these novel compounds, which are useful intermediates in forming 2-hydroxy-3,17β-estradiol derivatives.

DETAILED DESCRIPTION OF THE INVENTION

In accordance with the present invention, methods of synthesizing the foregoing novel compounds are provided. 2-alkoxy estradiols and a numbering system for identifying each carbon atom in the estradiol ring system are shown in the following structural formula:

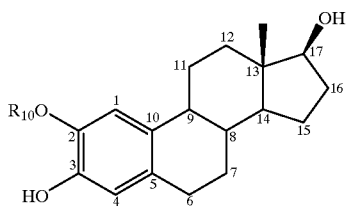

where $R_{10}$ is an alkyl group or a substituted alkyl group.

As used in the description, and in the claims, "alkyl" represents a straight-chain or branched hydrocarbon radical of 1 to 10 carbons in all its isomeric forms, such as methyl, ethyl, propyl, isopropyl, butyl, isobutyl, pentyl, etc. The alkyl group can optionally contain one or more double or triple bonds. The term "aryl" signifies a phenyl-, or an alkyl-, nitro- or halo-substituted phenyl group. The term "alkoxy" signifies the group alkyl-O—. Suitable substituents on an alkyl group or phenyl group include one or more halogens (e.g., fluoro, chloro, bromo and iodo), nitro, nitrile, —NH$_2$, —NH (alkyl), —NH (substituted alkyl), —N (alkyl)$_2$, —N(substituted alkyl)$_2$, carbonyl groups, —CONH$_2$, —CONH(alkyl), —CONH(substituted alkyl), CON(alkyl)$_2$, —CON(substituted alkyl)$_2$, —CO$_2$H, —COO(alkyl) and —COO (substituted alkyl). Halogenated alkyl groups can contain more than one kind of halogen. Examples of suitable alkyl or substituted alkyl groups include methyl, ethyl, n-propyl, iso-propyl, trifluoromethyl, trifluoroethyl, NO$_2$—CH$_2$—CH$_2$—, (CH$_3$)N—CH$_2$—CH$_2$—, —CH$_2$CH$_2$—CO—R', wherein $R_{10}$ is —H, alkyl, substituted alkyl, —OH, —O (alkyl), —O(substituted alkyl), —NH$_2$, —NH(alkyl), —NH (substituted alkyl), —N(substituted alkyl)$_2$ and —N(alkyl)$_2$.

The following reaction scheme depicts the production of 2-methoxyestra-3,17β-diol (5) by preparing a 2-boronyl or 2-silyl modified estradiol analog in accordance with the present invention. This synthesis is described in greater detail below.

Synthesis of 2-Methoxyestra-3,17β-diol

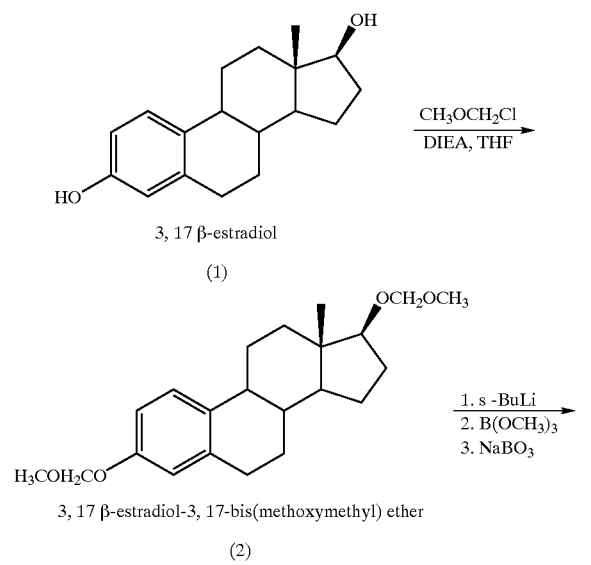

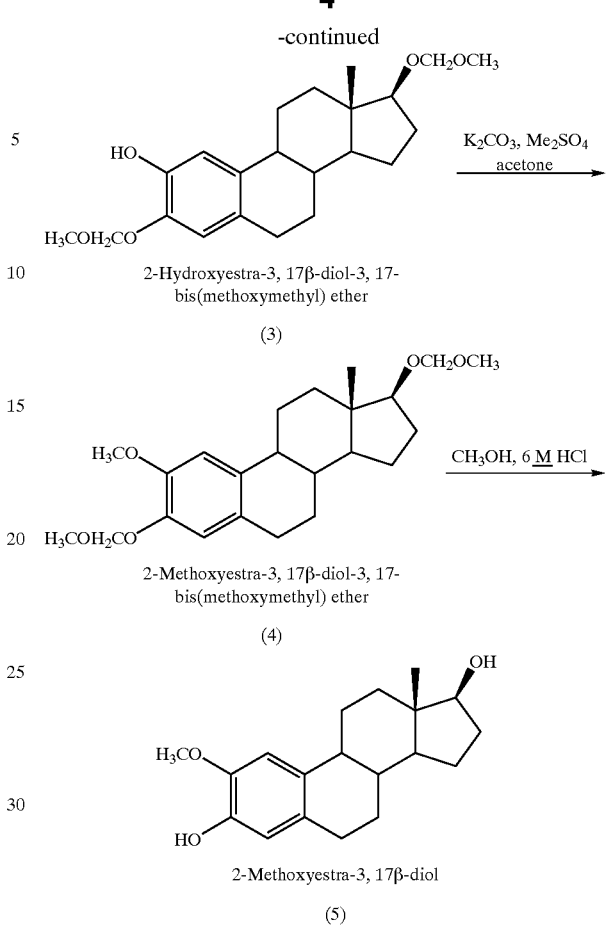

In accordance with the foregoing reaction scheme, a first intermediate (2) is prepared from 3,17β-estradiol (1) by protecting the two hydroxyl groups to form a compound represented by Structural Formula (I):

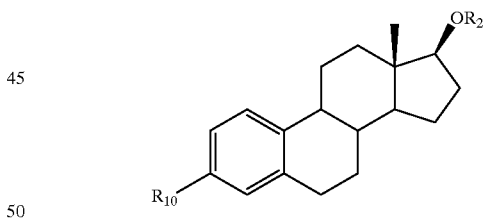

where $R_1$ and $R_2$ may be the same or different and each is independently a hydroxyl protecting group. As used herein, hydroxyl refers to alcohols and phenolic groups. A suitable "protecting group" is substantially inert with respect to the reagents used in the subsequent reactions in the disclosed synthesis of 2-alkoxy estradiols and does not cause, for example, undesired side reactions. Hydroxyl protecting groups are well known in the art and are described in, for example, Chapters 2 and 3 of Greene and Wuts, "Protective Groups in Organic Synthesis", John Wiley & Sons (1999), the entire disclosure of which is herein incorporated by reference. The skilled artisan can select suitable groups for use in the disclosed synthesis as well as conditions for applying and removing the hydroxyl protecting groups.

Preferably, $R_1$ is a protecting group that promotes ortho-lithiation at the 2-position. Such a protecting group contains an atom bearing a lone pair of electrons β to the hydroxyl oxygen. Such an atom is a heteroatom and preferably an oxygen atom. The general description of these types of ortho-directing protecting groups are substituted methyl ethers such as methoxymethyl, 2-methoxyethoxymethyl, 2-(trimethylsilyl)ethoxymethyl, tetrahydropyranyl, and tetrahydrofuranyl. Methoxymethyl is most preferred for its selective promotion of lithiation at the 2-position over the 4-position. Correspondingly, it is preferred that $R_1$ and $R_2$ are each methoxymethyl.

The first intermediate (2) is reacted with an organolithium reagent and a boron or a silicon reagent to form a second intermediate having Structural Formula (II) from the boron reagent or (III) from the silicon reagent:

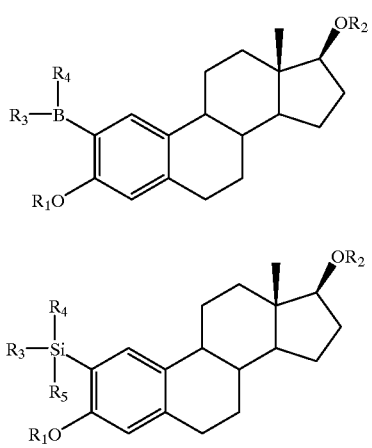

where $R_1$ and $R_2$ are as described above with respect to Structural Formula (I) and $R_3$, $R_4$ and $R_5$ are halogens, alkyl, aryl, hydroxy, substituted or unsubstituted alkoxy, or substituted or unsubstituted aryl.

Organolithium reagents are well known in the art. Examples of suitable organolithium reagents include methyllithium, n-butyllithium, sec-butyllithium, tert-butyllithium, or phenyllithium. Preferably, the organolithium reagent is sec-butyllithium. Reacting the first intermediate (2) with a 1 to 3 fold mole excess of organolithium reagent is preferred. A 1.5 fold mole excess of sec-butyllithium is most preferred.

The silicon and boron reagents are represented by Structural Formulae (IV) and (V) respectively:

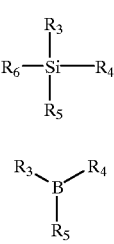

where $R_3$, $R_4$, $R_5$, and $R_6$ are halogens, alkyl, aryl, hydroxy, substituted or unsubstituted alkoxy, or substituted or unsubstituted aryl. The preferred silicon reagent is either dichlorodimethylsilane or diethoxydimethylsilane. Suitable boron reagents are tributyl borate, tripropyl borate, triisopropyl borate, triethyl borate, and trimethyl borate. The preferred boron reagent is trimethyl borate. Preferably, the first intermediate (2) is reacted with a 1 to 5 fold mole excess of either the silicon or boron reagent.

Suitable solvents for the organolithium and boron or silicon reactions include etheral solvents such as tetrahydrofuran (THF), dioxane, or glyme. THF is the preferred solvent. Suitable temperatures for carrying out the reaction typically are in the range of from about −110° C. to about 0° C. A reaction temperature below −70° C. is preferred.

The second intermediate is reacted with an oxidizing agent to form a third intermediate (3) having the Structural Formula (VI):

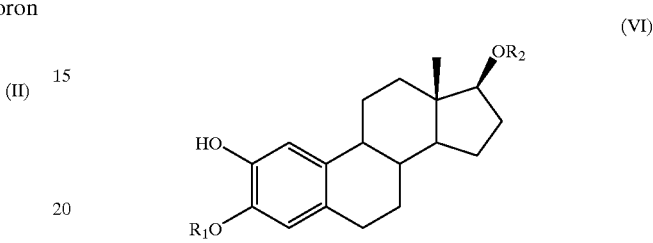

where $R_1$ and $R_2$ are as described above with respect to Structured Formula (I). Suitable oxidizing agents include peracetic acid, 3-chloroperoxybenzoic acid, tert-butyl hydroperoxide, magnesium monoperoxyphthalate, potassium peroxymonosulfate sold under the trademark OXONE®, hydrogen peroxide and sodium perborate. Sodium perborate is the preferred oxidizing agent.

A suitable biphasic solvent system for the oxidation reaction includes etheral solvents, such as THF, dioxane, or glyme, and water. THF and water is the preferred solvent system. A suitable THF-to-water ratio for the solvent system ranges from about 1:1 to about 1:5. Preferably, a 1:2 ratio of THF to water is used. A suitable temperature range for performing the oxidation reaction is between about 10° C. to about 35° C. Preferably, the oxidation reaction is performed at about room temperature.

Prior to oxidation, the boronyl (II) or silyl (III) second intermediate may be isolated. For example, quenching the borane reaction hydrolyzes the dialkoxy boronyl intermediate to form the boronic acid estradiol analog. Specifically, the boronyl modified estradiol analog represented by Structural Formula (VII) has been isolated:

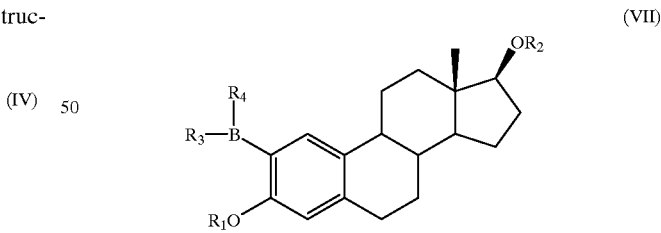

where $R_1$ and $R_2$ are each methoxymethyl and $R_3$ and $R_4$ are hydroxy groups. Specific conditions for quenching the borane reaction are provided in Example 3. Other modified estradiols include, but are not limited to, 2-trimethylsilyl, 2-chlorodimethylsilyl and 2-dimethylethoxysilyl. Preferably, the boronyl (II) or silyl (III) second intermediate remains in solution and is oxidized directly to form the third intermediate (3).

The 2-hydroxy group of the third intermediate (3) is "alkylated" to form a fourth intermediate (4) represented by Structural Formula (VIII):

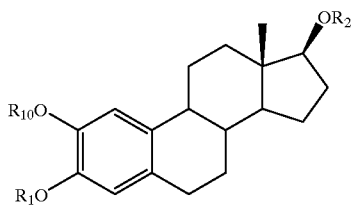

(VIII)

where $R_1$ and $R_2$ are as described above with respect to Structured Formula (I) and $R_{10}$ is a substituted or unsubstituted alkyl group. Preferably, $R_{10}$ is a methyl group. As used herein, "alkylation" refers to the removal of the phenolic proton under basic conditions and subsequent reaction of the phenoxide anion with an alkylating agent. The alkylation of phenols is well known in the art and can be accomplished by the "Williamson Reaction," for example. Specific conditions for alkylation are set forth in Example 3.

The hydroxyl protecting groups at the 3 and 17 positions of the fourth intermediate (4) are deprotected to form the desired 2-alkoxy estradiol represented by Structural Formula (IX):

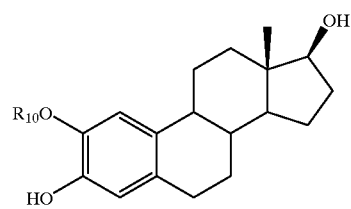

(IX)

$R_{10}$ is as described above. Suitable conditions for the removal of phenolic protecting groups are commonly known in the art and are disclosed in Chapters 2 and 3 of Green and Wuts, "Protective Groups in Organic Synthesis", John Wiley and Sons (1999). Specific conditions for deprotection are provided in Example 4.

The invention is illustrated by the following examples, which are not intended to be limiting in any way.

Experimental

EXAMPLE 1

3,17β-Estradiol-3,17-bis (methoxymethyl) Ether

To a solution of 3,17β-estradiol (120 g, 0.44 mol) in tetrahydrofuran (700 mL), under argon atmosphere, was added N,N-diisopropylethylamine (341.3 g, 2.64 mol) and chloromethyl methyl ether (171.1 g, 2.2 mol). The reaction was heated at 55±5° C. for 23.5 hours. The reaction was allowed to cool to less than 40° C. and then diluted with 20% aqueous ammonium chloride (300 mL). The mixture was stirred until the N,N-diisopropylethylamine hydrochloride precipitate dissolved. The layers were separated and the organic layer was extracted with 20% aqueous ammonium chloride (3×300 mL) and brine (1×300 mL) and concentrated in vacuo to give crude 3,17β-estradiol-3,17-bis (methoxymethyl) ether (159.1 g) as a clear orange viscous oil.

The crude material was purified on silica gel by radial compression chromatography using 16.7% ethyl acetate in hexanes to give 3,17β-estradiol-3,17-bis(methoxymethyl) ether (153.06 g, 96% yield) as a clear colorless oil: $^1$H NMR (DMSO-$d_6$) δ0.73 (s, 3H), 1.13–1.33 (m, 6H), 1.43–1.48 (m, 1H), 1.60–1.62 (m, 1H), 1.76–1.79 (m, 1H), 1.85–1.88 (m, 1H), 1.95–2.01 (m, 1H), 2.09–2.13 (m, 1H), 2.24–2.28 (m, 1H), 2.74 (m, 2H), 3.24 (s, 3H), 3.33 (s, 3H), 3.52 (t, J=8.4 Hz, 1H), 4.56 (dd, J=10.8, 6.5 Hz, 2H), 5.10 (m, 2H), 6.68 (d, J=2.5 Hz, 1H), 6.74 (dd, J=8.5, 2.6 Hz, 1H), 7.15 (d, J=8.6 Hz, 1H).

EXAMPLE 2

2-Hydroxyestra-3,17β-diol-3,17-bis(methoxymethyl) Ether

To a solution of 3,17β-estradiol-3,17-bis(methoxymethyl) ether (1169.8 g, 3.24 mol) in tetrahydrofuran (5850 mL) at −75° C., under argon atmosphere, was added sec-butyllithium (1.5 M in cyclohexane, 3750 mL, 5.63 mol) at a rate such that the reaction temperature did not exceed −65° C. The reaction was allowed to stir between −70° C. and −75° C. for two hours. Trimethyl borate (1450 mL, 12.9 mol) was added to the reaction at a rate such that the reaction temperature did not exceed −60° C. The reaction was allowed to stir between −70° C. and −75° C. for fifteen minutes and then allowed to warm to 0° C. The reaction was quenched with 10% (w/w) ammonium chloride in water (11,700 mL) and allowed to stir at ambient temperature for one hour. Sodium perborate tetrahydrate (1197.6 g, 12.9 mol) was added in portions to the solution at a rate such that the reaction temperature did not exceed 35° C. The reaction was allowed to stir at ambient temperature for fifteen hours and then filtered to remove the inorganic salts. The filter cake was washed with ethyl acetate (2×1000 mL) and the layers of the combined filtrates were separated. The aqueous layer was extracted with ethyl acetate (1×5000 mL). The combined organic layers were extracted with brine (1×5000 mL) and concentrated in vacuo. The resulting oil was dissolved in toluene (2000 mL), filtered to remove the precipitated inorganic salts, and then concentrated in vacuo to give 2-hydroxyestra-3,17β-diol-3,17-bis(methoxymethyl) ether (1121 g, 92% yield) as a viscous orange oil: $^1$H NMR (DMSO-$d_6$) δ6 0.74 (s, 3H), 1.15–1.35 (m, 6H), 1.46 (m, 1H), 1.61 (m, 1H), 1.75–1.78 (m, 1H), 1.87–1.89 (m, 1H), 2.0 (m, 1H), 2.06–2.13 (m, 2H), 2.64 (m, 2H), 3.25 (s, 3H), 3.38 (s, 3H), 3.51 (t, J=8.5 Hz, 1H), 4.58 (dd, J=10.5, 6.4 Hz, 2H), 5.05 (dd, J=9, 6.4 Hz, 2H), 6.67 (s,1H), 6.72 (s, 1H); MS, m/e 376 (M+).

EXAMPLE 3

2-Methoxyestra-3,17β-diol-3,17-bis (methoxymethyl) Ether

To a solution of 2-hydroxyestra-3,17β-diol-3,17-bis (methoxymethyl) ether (149.5 g, 0.397 mol) in acetone (775 mL), under argon atmosphere, was added powdered potassium carbonate (219.5 g, 1.59 mol) and dimethyl sulfate (75.1 g, 0.60 mol). The reaction was heated at reflux for 22.5 hours. The reaction was filtered through a bed of Celite and the filtrate was concentrated in vacuo to give 2-methoxyestra-3,17β-diol-3,17-bis(methoxymethyl) ether (155 g, 100 % yield) as a viscous orange oil.

EXAMPLE 4

2-Methoxyestra-3,17β-diol

A solution of 2-methoxyestra-3,17β-diol-3,17-bis (methoxymethyl) ether (36.6 g, 93.7 mmol) in tetrahydrofuran (55 mL) was added dropwise, over a period of ten minutes, to a solution of methanol (366 mL) and 6M hydrochloric acid (168 mL). The resulting mixture was allowed to stir at ambient temperature for 21 hours. The reaction was poured onto water (600 mL) with vigorous stirring. The resulting solid was isolated by suction filtration. The solid was washed with water (1200 mL) and dried in vacuo to give 2-methoxyestra-3,17β-diol (25 g, 88% yield) as a white solid.

While the invention has been described with respect to certain preferred embodiments, it will be understood that the invention is capable of numerous changes, modifications and rearrangements without departing from the scope of the claims.

What is claimed is:

1. A compound represented by the following structural formula:

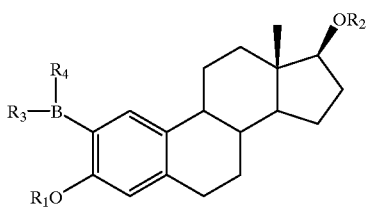

wherein $R_1$ and $R_2$ may be the same or different and represent a hydroxy-protecting group and $R_3$ and $R_4$ are selected from the group consisting of halogen, alkyl, aryl, hydroxy, substituted or unsubstituted alkyl, and substituted or unsubstituted aryl.

2. The compound of claim 1 wherein $R_1$ and $R_2$ are each methoxymethyl.

3. The compound of claim 2 wherein $R_3$ and $R_4$ are each a hydroxy group.

4. A method of synthesizing a 2-boronyl estradiol having the following structural formula:

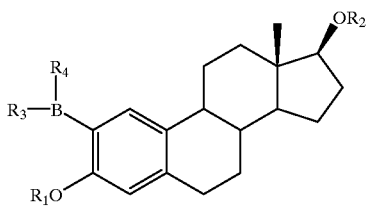

wherein $R_1$ and $R_2$ may be the same or different and represent a hydroxy-protecting group said method comprising the step of:

reacting a precursor compound represented by the following structural formula:

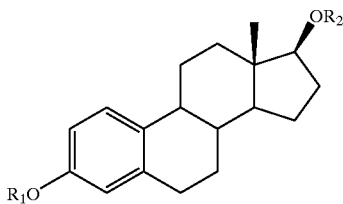

with an organolithium reagent and a boron reagent, said boron reagent having the following structural formula:

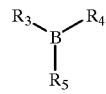

wherein $R_3$, $R_4$ and $R_5$ are selected from the group consisting of halogen, alkyl, aryl, hydroxy, substituted or unsubstituted alkyl, and substituted or unsubstituted aryl.

5. The method of claim 4 wherein $R_1$ and $R_2$ are methoxymethyl.

6. The method of claim 4 wherein said boron reagent is selected from the group consisting of tributyl borate, tripropyl borate, triisopropyl borate, triethyl borate and trimethyl borate.

7. The method of claim 4 wherein said organolithium reagent is selected from the group consisting of methyllithium, n-butyllithium, sec-butyllithium, tert-butyllithium and phenyllithium.

8. The method of claim 4 wherein said reaction occurs in an etheral solvent selected from the group consisting of tetrahydrofuran, dioxane and glyme.

9. The method of claim 4 wherein $R_3$ and $R_4$ are each a hydroxy group.

* * * * *

UNITED STATES PATENT AND TRADEMARK OFFICE
CERTIFICATE OF CORRECTION

PATENT NO.    : 6,448,419 B1
DATED         : September 10, 2002
INVENTOR(S)   : Herbert E. Paaren et al.

It is certified that error appears in the above-identified patent and that said Letters Patent is hereby corrected as shown below:

<u>Title page,</u>
Item [56], References Cited, please add the following references:

-- U.S. PATENT DOCUMENTS

| | | | |
|---|---|---|---|
| 6,051,726 | 4/2000 | Sachdeva et al. | 552/614 |
| 6,054,598 | 4/2000 | Sachdeva et al. | 552/627 |
| 6,136,992 | 10/2000 | Ram et al. | 552/614 |

OTHER PUBLICATIONS

Kabalka, George W. et al., "Sodium Perborate: A Mild and Convenient Reagent for Efficiently Oxidizing Organoboranes," J. Org. Chem., Vol. 54, No. 25, 1989, pp. 5930-5933.

Simon, Jurgen et al., "Regioselective Conversion of Arylboronic Acids to Phenols and Subsequent Coupling to Symmetrical Diaryl Ethers," J. Org. Chem., Vol. 66, No. 2, 2001, pp. 633-634.

Brown Ripin, David H. et al., "A safe, scaleable method for the oxidation of carbon-boron bonds with Oxone," Tetrahedron Letters 41 (2000), pp. 5817-5819.

Kabalka, George W. et al., "Sodium Perborate: A Mild and Convenient Reagent For Efficiently Oxidizing Trialkylboranes," Tetrahedron Letters, Vol. 30, No. 12, (1989), pp. 1483-1486, Pergamon Press plc.

Pert, Derek J. et al., "An Alternative Route to 2-Bromo- and 2-Iodo-estradiols from Estradiol," Aust. J. Chem., Vol. 40, 1987, pp. 303-309.

Lovely, Carl J. et al., "2-(Hydroxyalkyl)estradiols: Synthesis and Biological Evaluation," Journal of Medicinal Chemistry, Vol. 39, No. 9, 1996, pp. 1917-1923.

Cushman, Mark et al., "Synthesis of Analogs of 2-Methyoxyestradiol with Enhanced Inhibitory Effects on Tubulin Polymerization and Cancer Cell Growth," Journal of Medicinal Chemistry, Vol. 40, No. 15, 1997, pp. 2323-2334.

Amato, J. S. et al., "A New Preparation of Chloromethyl Methyl Ether Free of Bis[chloromethyl] Ether," Synthesis, Communications, Georg Thieme Publishers, December 1979, pp. 970-971.

Parker, Kathlyn A. et al., "Directed Hydroxylation of Aromatics," J. Org. Chem., Vol. 52, No. 4, 1987, pp. 674-676.

Mino, Takashi et al., "Synthesis of Lactones by Baeyer - Villiger Oxidation with Magnesium Monoperphthalate Hexahydrate," J. Org. Chem., Vol. 62, No. 8, 1997, pp. 2633-2635. --

UNITED STATES PATENT AND TRADEMARK OFFICE
CERTIFICATE OF CORRECTION

PATENT NO.   : 6,448,419 B1
DATED        : September 10, 2002
INVENTOR(S)  : Herbert E. Paaren et al.

It is certified that error appears in the above-identified patent and that said Letters Patent is hereby corrected as shown below:

Column 1,
Line 67, insert after the structural formula -- (If a boron reagent) --.

Column 2,
Line 11, delete "(If a boron reagent)".
Line 31, delete "(silicon reagent) and (boron reagent)".

Column 4,
Formula (I), that portion of the formula reading "$R_{10}$" should read -- $R_1O$ --

Column 5,
Line 42, delete "butylithium" and insert therefor -- butyllithium --.
Line 43, delete "sec-butylithium" and insert therefor -- sec-butyllithium --.

Column 8,
Line 17, delete "1.5 M" and insert therefor -- 1.5 $\underline{M}$ --.
Line 41, delete "δ6" and insert therefor -- δ --.

Column 9,
Line 2, delete "6M" and insert therefor -- 6$\underline{M}$ --.

Signed and Sealed this

Twenty-fourth Day of December, 2002

JAMES E. ROGAN
*Director of the United States Patent and Trademark Office*